United States Patent [19]
Hernandez

[11] Patent Number: 5,806,524
[45] Date of Patent: Sep. 15, 1998

[54] MALE CONDOM DEVICE WITH IMPROVED ADHESIVITY AND METHOD FOR MANUFACTURING

[76] Inventor: Arturo Rafael Hernandez, 1918 First Ave. Draper Hall Box 263, New York, N.Y. 10029

[21] Appl. No.: 947,763

[22] Filed: Oct. 10, 1997

[51] Int. Cl.$^6$ ........................................................ A61F 6/04
[52] U.S. Cl. ............................................ 128/844; 128/918
[58] Field of Search ................................... 128/842, 844, 128/918; 604/347–353

[56] References Cited

U.S. PATENT DOCUMENTS

| | | | |
|---|---|---|---|
| 2,604,092 | 7/1952 | Brown | 128/844 |
| 4,863,449 | 9/1989 | Therriault | 128/844 |
| 4,888,007 | 12/1989 | Loeb | 128/844 |
| 5,137,032 | 8/1992 | Harmon | 128/844 |
| 5,579,784 | 12/1996 | Harari | 128/844 |

*Primary Examiner*—Michael A. Brown
*Attorney, Agent, or Firm*—Cooper & Dunham LLP

[57] ABSTRACT

A condom with improved adhesivity and a method for manufacturing same includes the steps of placing a pre-rolled condom on a distal end of a tubular fixture, unrolling the condom towards a proximal end of the tubular fixture leaving a rolled portion equal to a distance X+Y, holding the condom a distance X from the rolled portion using a flexible ring-shaped holding fixture forming a first portion, folding the first portion over the flexible ring-shaped holding fixture so that the rolled portion is placed a distance X from the flexible ring-shaped holding fixture, applying an adhesive layer on the folded first portion between the rolled portion and the flexible ring-shaped holding fixture, unrolling the rolled portion a distance X over the first portion having the adhesive layer thereon forming a ply portion and a distance Y over the tubular fixture, thereby completely unrolling the rolled portion, removing the flexible ring-shaped holding fixture, and rolling the condom back fully towards the distal end of the tubular fixture. The condom with improved adhesivity includes an elongated hollow tubular condom body closed at a distal end and made of a flexible material, wherein a proximal end of the tubular body includes a ply portion with an adhesive layer therebetween, and wherein the ply portion is followed to an opening in the proximal end by a final portion without adhesive, whereby when the final portion is pulled during application the ply portion is unfolded resulting in the adhesive layer being positioned between the condom body and the penis of the user.

14 Claims, 3 Drawing Sheets

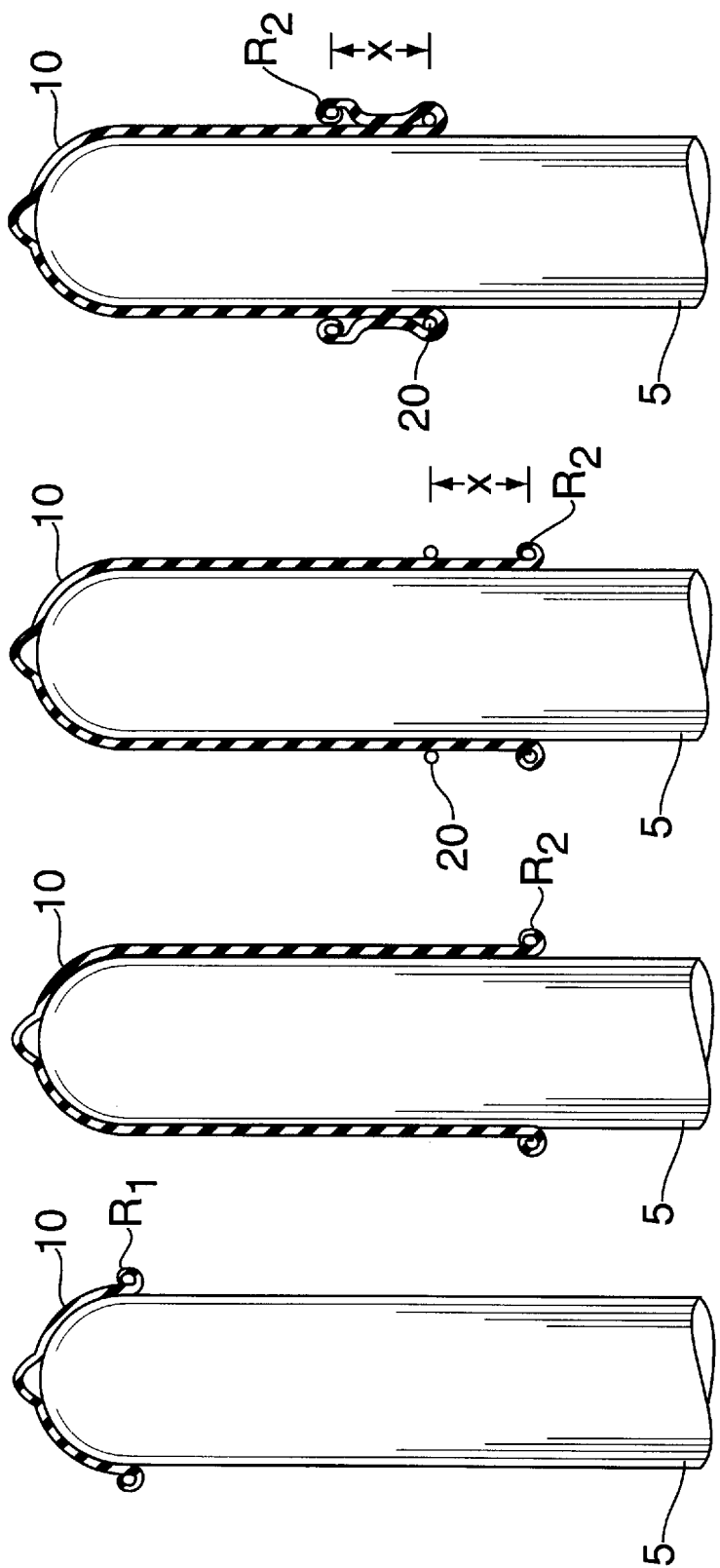

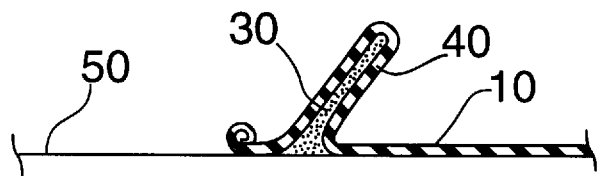
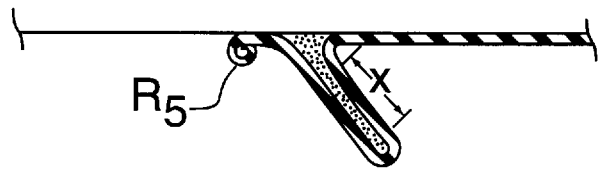
FIG. 9
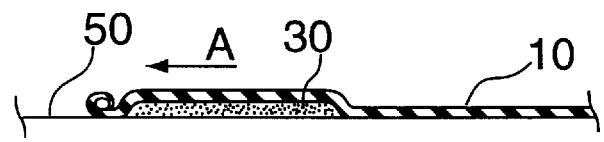
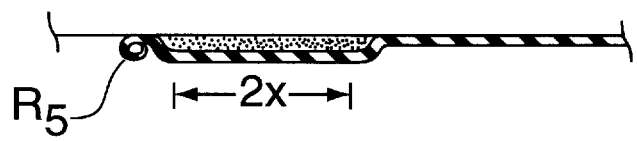
FIG. 10
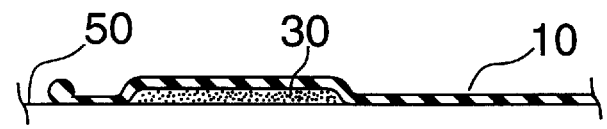
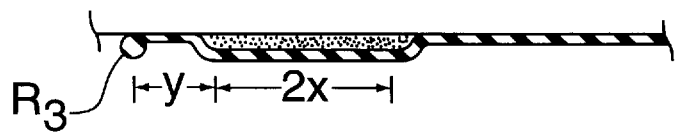
FIG. 11

MALE CONDOM DEVICE WITH IMPROVED ADHESIVITY AND METHOD FOR MANUFACTURING

FIELD OF THE INVENTION

The present invention relates to a condom with improved adhesivity and a method for manufacturing same. More particularly, the condom of this invention has a folded section with an adhesive layer in the fold, whereby when the folded section is pulled during application it is unfolded placing an adhesive layer between the condom and the penis of the user.

BACKGROUND OF THE INVENTION

Condoms or prophylactic devices are used for preventing pregnancy and the transmission of sexually transmitted diseases, including AIDS.

According to the patent literature, modern condom designs are intended to achieve some sort of sealant or engagement relationship with the penis, for preventing spillage of semen or for preventing slippage during vigorous intercourse, for example.

The following patents have been found to be relevant to the field of the present invention:

(1) U.S. Pat. No. 5,421,350 ("Friedman"),
(2) U.S. Pat. No. 5,069,228 ("Sorkin"),
(3) Des. U.S. Pat. No. 252,949 ("Okamoto"),
(4) U.S. Pat. No. 4,869,269 ("Sharkan"),
(5) U.S. Pat. No. 4,917,113 ("Conway")
(6) U.S. Pat. No. 5,137,032 ("Harmon"), and
(7) U.S. Pat. No. 5,513,654 ("Delson").

A problem with current condom designs is that they slip off because of poor adhesion characteristics, and condoms which include adhesives have cumbersome designs like the pubic shield with an adhesive to adhere to the pubic area described in Sorkin '228, for example.

OBJECTS AND SUMMARY OF THE INVENTION

The present invention is intended to overcome the above problems and consists of a condom with a ply portion having an adhesive layer therebetween and a method of manufacturing same.

Accordingly, it is an object of the present invention to provide an condom with improved adhesivity that will not slip off during use.

In accordance with one aspect of the present invention a method for manufacturing a condom with improved adhesivity includes the steps of placing a pre-rolled condom on a distal end of a tubular fixture, unrolling the condom towards a proximal end of the tubular fixture leaving a rolled portion equal to a distance X+Y, holding the condom a distance X from the rolled portion using a flexible ring-shaped holding fixture forming a first portion, folding the first portion over the flexible ring-shaped holding fixture so that the rolled portion is placed a distance X from the flexible ring-shaped holding fixture, applying an adhesive layer on the folded first portion between the rolled portion and the flexible ring-shaped holding fixture, unrolling the rolled portion a distance X over the first portion having the adhesive layer thereon forming a ply portion and a distance Y over the tubular fixture, thereby completely unrolling the rolled portion, removing the flexible ring-shaped holding fixture, and rolling the condom back fully towards the distal end of the tubular fixture.

In accordance with another aspect of the present invention a condom with improved adhesivity is provided including an elongated hollow tubular condom body closed at a distal end and made of a flexible material, wherein a proximal end of said tubular body includes a ply portion with an adhesive layer therebetween, and wherein said ply portion is followed to an opening in the proximal end by a final portion without adhesive, whereby when said final portion is pulled during application said ply portion is unfolded resulting in said adhesive layer being positioned between the condom body and the penis of the user.

These and other objects, advantages, and features of the present invention will become apparent to those skilled in the art upon consideration of the following description of the present invention.

BRIEF DESCRIPTION OF THE DRAWINGS

FIG. 1 shows a first step of the method for manufacturing a condom according to an embodiment of the present invention;

FIG. 2 shows a second step of the method for manufacturing a condom according to an embodiment of the present invention;

FIG. 3 shows a third step of the method for manufacturing a condom according to an embodiment of the present invention;

FIG. 4 shows a fourth step of the method for manufacturing a condom according to an embodiment of the present invention;

FIG. 9 shows the condom partially unrolled over the penis shaft according to an embodiment of the present invention;

FIG. 10 shows the condom partially unrolled over the penis shaft after being pulled to expose a layer of adhesive according to an embodiment of the present invention; and FIG. 11 shows the condom fully unrolled over the penis shaft according to an embodiment of the present invention.

DETAILED DESCRIPTION OF THE INVENTION

Figure 8:
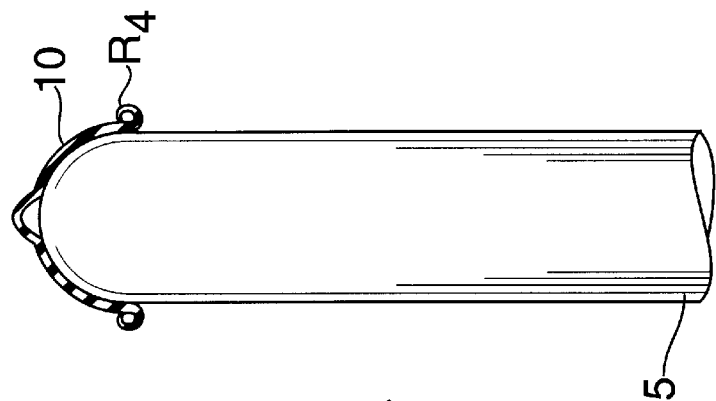
FIG. 8 shows an eighth step of the method for manufacturing a condom according to an embodiment of the present invention.

While this invention is susceptible of embodiment in many different forms, there is shown in the drawings and will herein be described in detail specific embodiments, with the understanding that the present disclosure is to be considered as an example of the principles of the invention and not intended to limit the invention to the specific embodiments shown and described. In the description below, like reference numerals are used to described the same, similar or corresponding parts in the several views of the drawings.

Turning now to FIGS. 1–8 a method of manufacturing a condom with improved adhesivity according to an embodiment of the present invention will be described.

The method utilizes a tubular fixture 5 with a rounded tip to facilitate placing a standard pre-rolled condom 10 on its tip, as shown in FIG. 1. The pre-rolled condom 10 has a rolled portion $R_1$, and is shown as a cross-section in the drawings for clarity.

After placing the condom 10 on the fixture 5, the condom 10 is partially unrolled, as shown in FIG. 2, over the fixture 5 leaving a rolled portion $R_2$ equal to X+Y cm. In the preferred embodiment, X is approximately 1 cm and Y is approximately 0.5 cm making the rolled condom portion $R_2$ equal to 1.5 cm.

Next, as shown in FIG. 3, a flexible ring-shaped holding fixture 20 is placed a distance X from the rolled portion $R_2$ forming a first portion therebetween. In the preferred embodiment, the flexible ring-shaped holding fixture 20 is a rubber band and the distance X is 1 cm.

In the following step, shown in FIG. 4, the first portion formed between the rolled portion $R_2$ and the flexible ring-shaped holding fixture 20 is folded over the ring-shaped holding fixture 20 placing the rolled portion $R_2$ a distance X from the flexible ring-shaped holding fixture 20, a shown in FIG. 4, X being 1 cm in the preferred embodiment.

Figure 5:
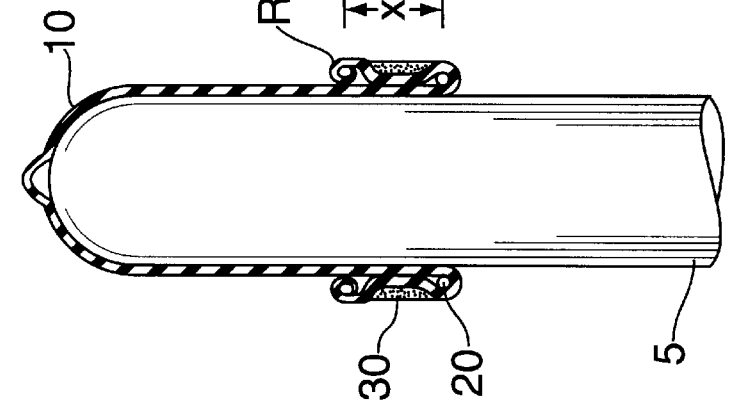
FIG. 5 shows a fifth step of the method for manufacturing a condom according to an embodiment of the present invention.

In a further step, shown in FIG. 5, a layer of adhesive 30 is applied to the folded first portion between the rolled portion $R_2$ and the flexible ring-shaped holding fixture 20. In the preferred embodiment a medical adhesive comprised of polydimethylsiloxane in trichloro-trifluoroethane solvent with a hydroflurocarbon 152A propellant is used. The adhesive 30 of the preferred embodiment is a medical adhesive used for ostomy and other appliances and can be purchased from Hollister, Inc., 2000 Hollister Drive, Libertyville, Ill. 60048, but other medical adhesives can be used. In the preferred embodiment the adhesive 30 is sprayed covering the entire first portion but covering only sections of the first portion with the adhesive is also acceptable.

Figure 6:
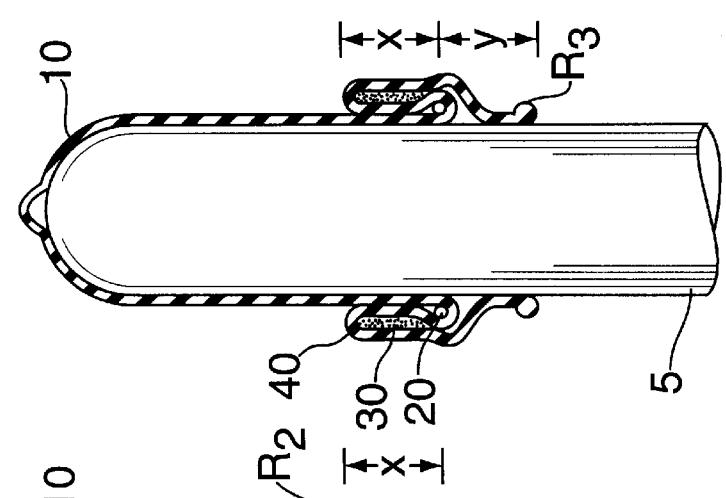
FIG. 6 shows a sixth step of the method for manufacturing a condom according to an embodiment of the present invention.

In a further step, shown in FIG. 6, the rolled portion $R_2$ is completely unrolled over the adhesive layer 30 and the tubular fixture 5. As shown in FIG. 6, since the rolled portion $R_2$ has a length of X+Y and the adhesive layer 30 has a length of X, when the rolled portion $R_2$ is unrolled a ply portion 40 with adhesive therebetween is formed having a length of X and the rest of the condom having a length of Y is unrolled over the tubular fixture 5. After unrolling the condom, a ring $R_3$ usually remains and is part of standard condoms. Again, in the preferred embodiment the ply portion 40 has length of X=1 cm, and the length unrolled over the tubular fixture 5 is Y=0.5 cm.

Figure 7:
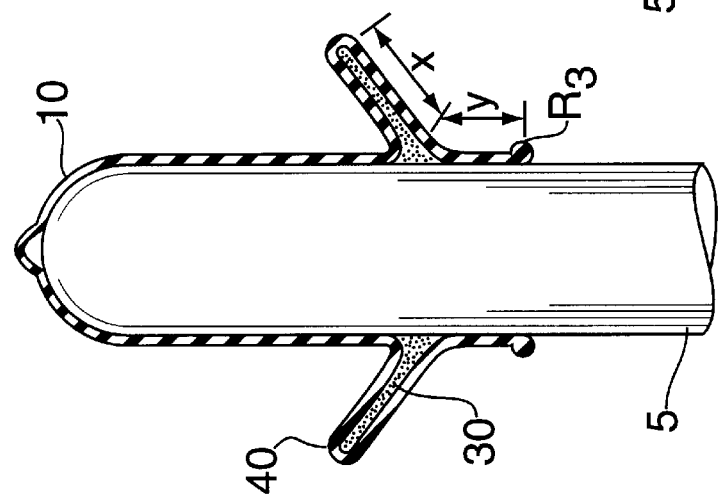
FIG. 7 shows a seventh step of the method for manufacturing a condom according to an embodiment of the present invention.

Next, the flexible ring-shaped holding fixture 20 is removed and the structure of this novel condom can be appreciated as shown in FIG. 7.

In a final step, as shown in FIG. 8, the condom is rolled back fully towards the top of the fixture leaving the ply portion 40 undisturbed inside the rolled portion $R_4$ until the condom is applied. At this moment, the condom is ready to be packaged and distributed.

Turning now to FIGS. 9–11, the use of this novel condom with improved adhesivity will be described.

The condom 10 is placed over the erect penis of the user 50 and is unrolled until the ply portion 40 is uncovered, as shown in FIG. 9, a rolled final portion $R_5$ of a length Y will remain. At this moment, this rolled portion $R_5$ is pulled as shown by the arrow A in FIG. 10 unfolding the ply portion and positioning the adhesive layer 30 between the condom body 10 and the penis of the user 50, as shown in FIG. 10. The adhesive layer will have a length of 2× or 2 cm in the preferred embodiment. In the final step, the rolled portion $R_5$ is fully unrolled, as shown in FIG. 11, leaving a final portion of a length Y without adhesive ending in the ring $R_3$.

The above description is based on a particular embodiment of the invention, but it will be apparent that many modifications variations could be effected by one skilled in the art without departing from the spirit of the invention.

Thus, it is apparent that in accordance with the present invention an apparatus and method that fully satisfies the objectives, aims, and advantages is set forth above. While the invention has been described in conjunction with specific embodiments, it is evident that many alternatives, modifications, permutations, and variations will become apparent to those skilled in the in art light of the foregoing description. Accordingly, it is intended that the present invention embrace all such alternatives, modifications and variations as fall within the scope of the appended claims.

I claim:

1. A method for manufacturing a condom with improved adhesivity comprising the steps of:

placing a pre-rolled condom on a distal end of a tubular fixture;

unrolling the condom towards a proximal end of the tubular fixture leaving a rolled portion equal to a distance X+Y;

holding the condom a distance X from the rolled portion using a flexible ring-shaped holding fixture so as to form a first portion;

folding the first portion over the flexible ring-shaped holding fixture so that the rolled portion is placed a distance X from the flexible ring-shaped holding fixture;

applying an adhesive layer on the folded first portion between the rolled portion and the flexible ring-shaped holding fixture;

unrolling the rolled portion a distance X over the first portion having the adhesive layer thereon forming a ply portion and a distance Y over the tubular fixture, thereby completely unrolling the rolled portion;

removing the flexible ring-shaped holding fixture; and rolling the condom back fully towards the distal end of the tubular fixture.

2. The method as recited in claim 1, wherein the distance X is 1 cm.

3. The method as recited in claim 2, wherein the distance Y is 0.5 cm.

4. The method as recited in claim 3, wherein the flexible ring-shaped holding fixture is a rubber band.

5. The method as recited in claim 4, wherein the step of applying an adhesive layer consists of spraying a medical adhesive comprised of polydimethylsiloxane in trichloro-trifluroethane solvent with hydrofluorocarbon 152A propellant.

6. The method as recited in claim 5, wherein the step of applying an adhesive layer applies the adhesive on a plurality of sections of the first portion.

7. A condom with improved adhesivity, comprising:

an elongated hollow tubular condom body closed at a distal end and made of a flexible material, wherein a proximal end of said tubular body includes a ply portion formed of two substantially parallel layers with an adhesive layer between said two substantially parallel layers, and wherein said ply portion extends outwardly from said tubular body and is followed in a direction toward an opening in the proximal end of the body by a final portion without adhesive, whereby when said final portion is pulled during application said ply portion is unfolded resulting in said adhesive layer being positioned between the condom body and the penis of the user.

8. The condom as recited in claim 7, wherein the adhesive is comprised of polydimethylsiloxane in trichloro-trifluorethane solvent with hydrofluorocarbon 152A propellant.

9. The condom as recited in claim 8, wherein said ply portion is 1 cm.

10. The condom as recited in claim 9, wherein said final portion is 0.5 cm.

11. The condom as recited in claim 10, wherein said adhesive layer includes a first plurality of adhesive sections separated by a second plurality of sections without adhesive.

12. The condom as recited in claim 7, wherein said condom body is coated with a spermicide.

13. The condom as recited in claim 7, wherein said flexible material is latex.

14. A condom with improved adhesivity, comprising:
an elongated hollow tubular condom body closed at a distal end and made of a flexible material, wherein a proximal end of said tubular body includes a ply portion with an adhesive layer between plies thereof, and wherein said ply portion is followed in a direction toward an opening in the proximal end of the body by a final portion without adhesive, whereby when said final portion is pulled during application said ply portion is unfolded resulting in said adhesive layer being positioned between the condom body and the penis of the user, wherein the adhesive is comprised of polydimethylsiloxane in trichloro-trifluorethane solvent with hydrofluorocarbon 152A propellant.

* * * * *